United States Patent
Downer et al.

(10) Patent No.: US 8,105,332 B2
(45) Date of Patent: Jan. 31, 2012

(54) LENS DELIVERY SYSTEM

(75) Inventors: David A. Downer, Fort Worth, TX (US); Dengzhu Yan, Arlington, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/928,554

(22) Filed: Oct. 30, 2007

(65) Prior Publication Data

US 2009/0112223 A1 Apr. 30, 2009

(51) Int. Cl.
*A61F 9/00* (2006.01)

(52) U.S. Cl. ...... 606/107; 623/6.12

(58) Field of Classification Search ........ 623/6.12; 606/107

See application file for complete search history.

(56) References Cited

U.S. PATENT DOCUMENTS

| | | |
|---|---|---|
| 4,681,102 A | 7/1987 | Bartell |
| 5,275,604 A | 1/1994 | Rheinish et al. |
| 5,494,484 A * | 2/1996 | Feingold ............. 606/107 |
| 5,499,987 A * | 3/1996 | Feingold ............. 606/107 |
| 5,616,148 A | 4/1997 | Eagles et al. |
| 5,620,450 A | 4/1997 | Eagles et al. |
| 5,643,276 A * | 7/1997 | Zaleski ............... 606/107 |
| 5,653,715 A | 8/1997 | Reich et al. |
| 6,899,698 B2 * | 5/2005 | Sams ................. 604/211 |
| 7,217,274 B2 * | 5/2007 | Meyer ................ 606/107 |
| 7,357,426 B2 * | 4/2008 | Bormioli ............. 285/314 |
| 2004/0097954 A1 * | 5/2004 | Meyer ................ 606/107 |
| 2006/0235429 A1 | 10/2006 | Lee et al. |
| 2008/0086146 A1 * | 4/2008 | Ishii et al. ........... 606/107 |
| 2008/0119865 A1 * | 5/2008 | Meunier et al. ....... 606/107 |

FOREIGN PATENT DOCUMENTS

| | | |
|---|---|---|
| EP | 1832247 | 9/2007 |
| EP | 1941846 | 7/2008 |
| WO | WO 2007/037223 | 4/2007 |

* cited by examiner

*Primary Examiner* — Ryan Severson
*Assistant Examiner* — Julie A Szpira
(74) *Attorney, Agent, or Firm* — Jonathan Prejean

(57) ABSTRACT

A lens delivery system handpiece having a threaded plunger rod with a ball lock ring. Locking the ring causes the plunger to be advanced by turning a thumbscrew or knob. Unlocking the ring allows the plunger to be advanced by pushing on the thumbscrew or knob in a manner similar to a syringe.

3 Claims, 4 Drawing Sheets

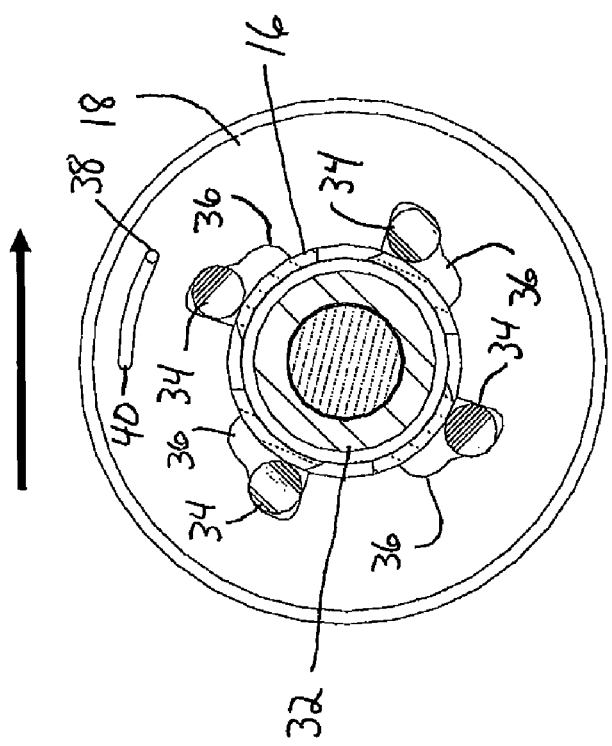
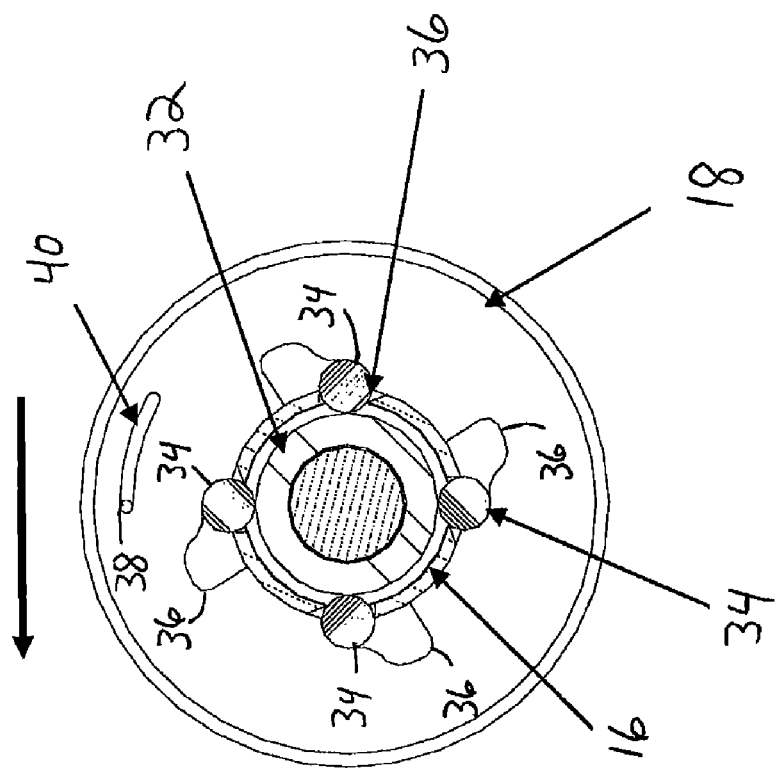
FIG. 3
FIG. 2

LENS DELIVERY SYSTEM

This invention relates to intraocular lenses (IOLs) and more particularly to devices used to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. The most commonly used injector cartridge design is illustrated in U.S. Pat. No. 4,681,102 (Bartell), and includes a split, longitudinally hinged cartridge. Similar designs are illustrated in U.S. Pat. Nos. 5,494,484 and 5,499,987 (Feingold) and 5,616,148 and 5,620,450 (Eagles, et al.). In an attempt to avoid the claims of U.S. Pat. No. 4,681,102, several solid cartridges have been investigated, see for example U.S. Pat. No. 5,275,604 (Rheinish, et al.) and U.S. Pat. No. 5,653,715 (Reich, et al.).

The handpieces used with prior art cartridges generally push the lens through the cartridge using a plunger. The plunger is either pushed but the user (similar to a syringe) or is threaded and is advanced by turning a thumbwheel. Surgeon preference generally dictates which style handpiece is used but it is advantageous that a single handpiece contain a mechanism that allows both typed of movement.

Accordingly, a need continues to exist for a lens delivery system handpiece having a plunger that can be advanced by pushing or by turning of a thumbscrew.

BRIEF SUMMARY OF THE INVENTION

The present invention improves upon prior art by providing a lens delivery system handpiece having a threaded plunger rod with a ball lock ring. Locking the ring causes the plunger to be advanced by turning a thumbscrew or knob. Unlocking the ring allows the plunger to be advanced by pushing on the thumbscrew or knob in a manner similar to a syringe.

It is accordingly an object of the present invention to provide a lens delivery system having a handpiece with a locking ring.

It is a further object of the present invention to provide a lens delivery system having a handpiece with a plunger that can be advanced by pushing or turning a knob.

Other objectives, features and advantages of the present invention will become apparent with reference to the drawings, and the following description of the drawings and claims.

BRIEF DESCRIPTION OF THE DRAWINGS

FIG. 2 is a cross-sectional view of the ball lock ring of the handpiece illustrated in FIG. 1 showing the lock ring in the locked position.

FIG. 3 is a cross-sectional view of the ball lock ring of the handpiece illustrated in FIG. 1 showing the lock ring in the unlocked position.

DETAILED DESCRIPTION OF THE INVENTION

Figure 1:
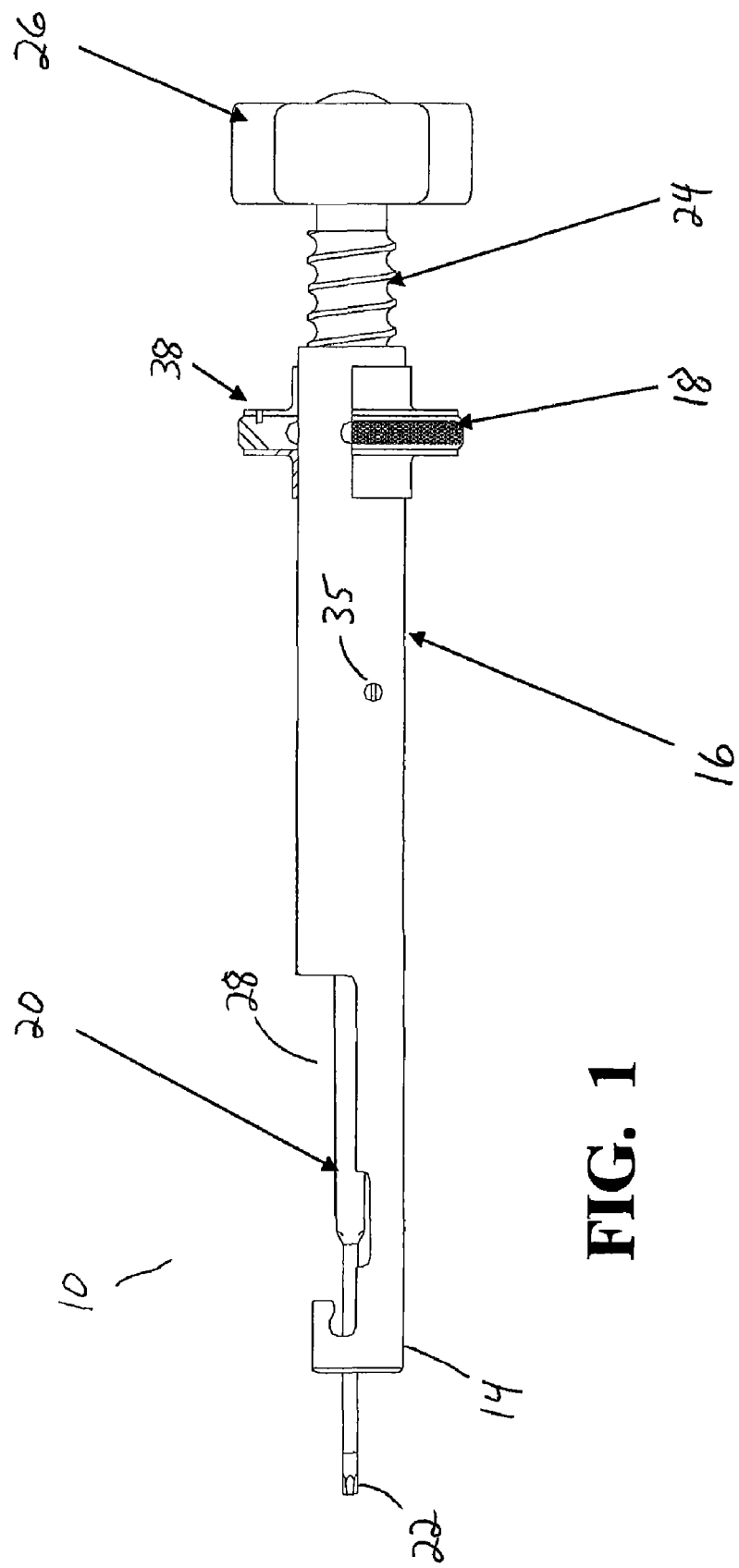
FIG. 1 is a side elevational view of the handpiece of the lens delivery system of the present invention.
Figure 4:
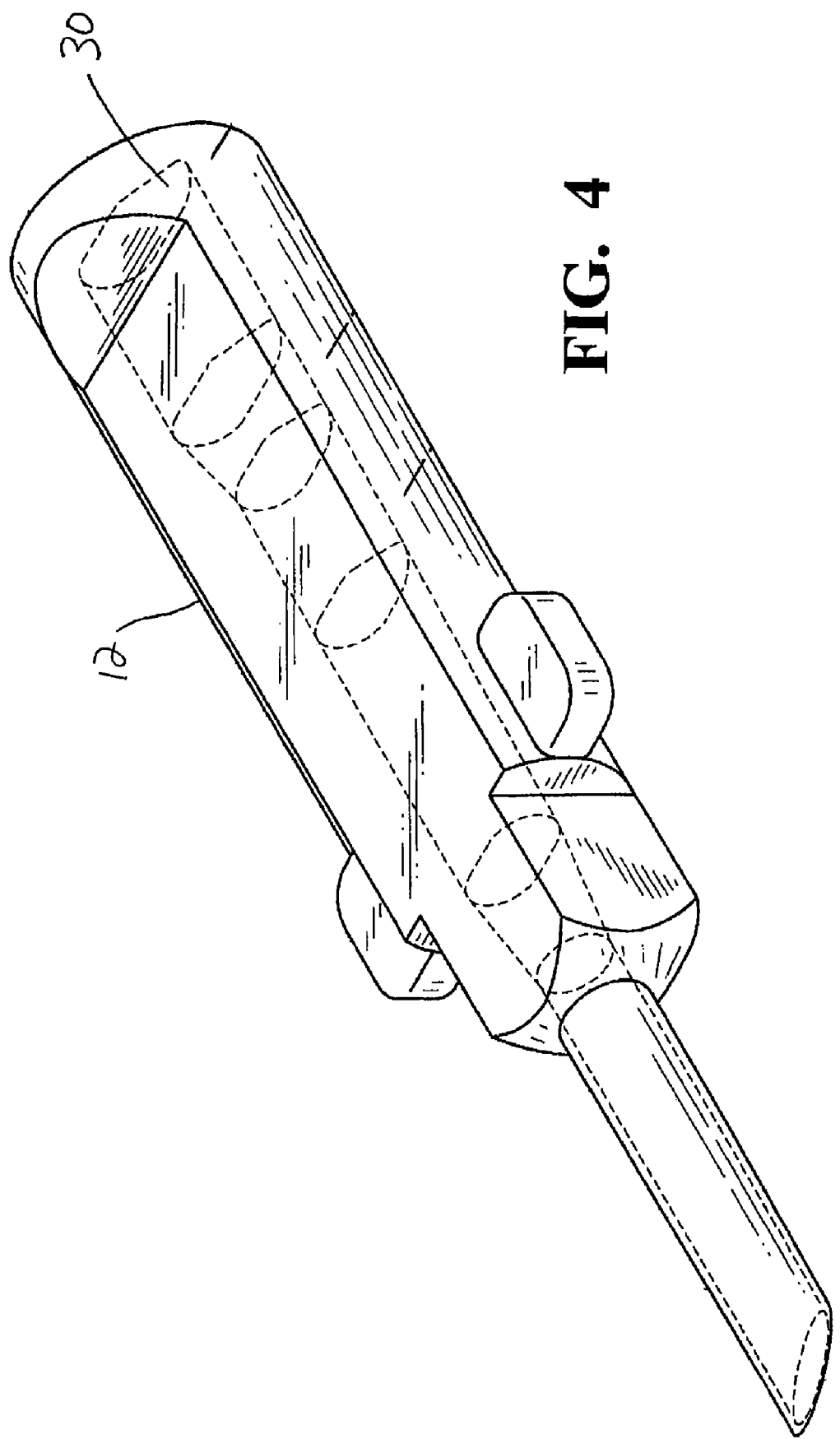
FIG. 4 is a perspective view of a cartridge that may be used with the lens delivery system of the present invention.
Figure 5:
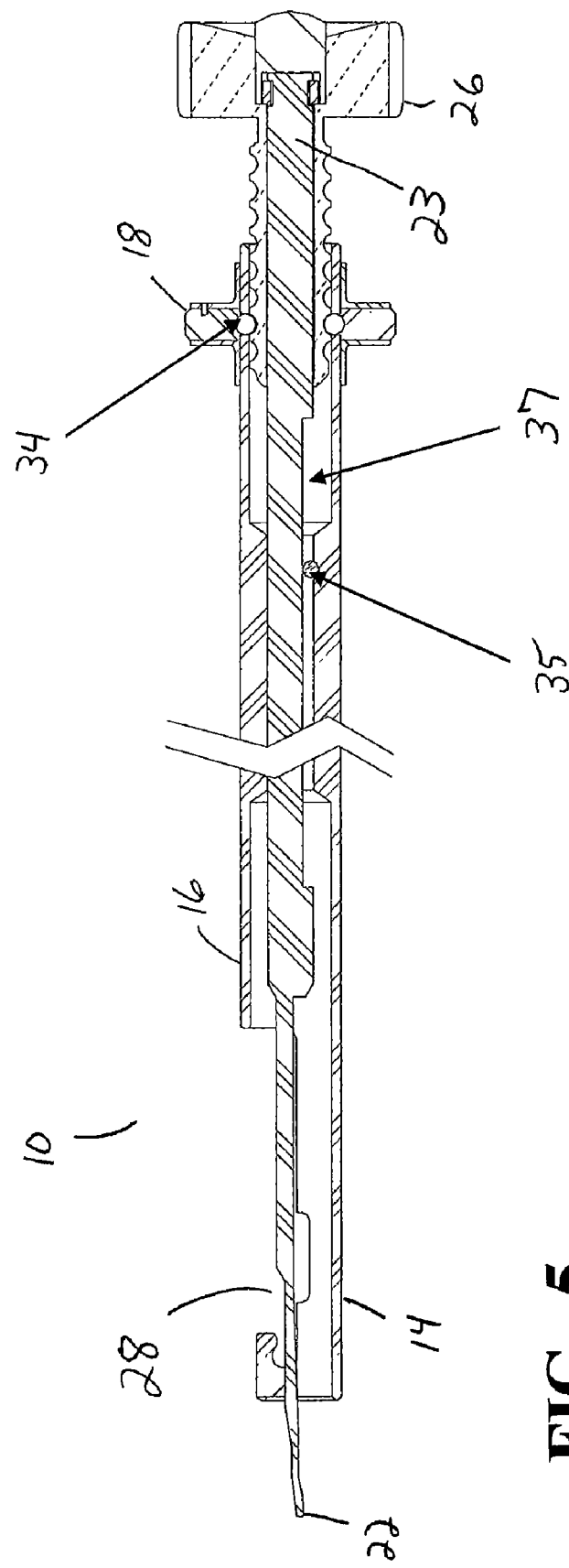
FIG. 5 is a cross-section view of the handpiece of the lens delivery system of the present invention.

As best seen in FIGS. 1 and 4, lens delivery system 10 of the present invention generally includes cartridge 12 and handpiece 14. Handpiece 14 generally consists of barrel 16, ball lock ring 18 (shown in FIG. 1 in partial cross-section) and plunger rod 20. As best seen in FIGS. 1 and 5, plunger rod 20 contains distal tip 22 and proximal end 23 which is rotationally journaled into grooved outer shaft 24 so that outer shaft 24 spins freely on proximal end 23 of plunger rod 20. Rigidly attached to outer shaft 24 is knob 26. Pin 35 fits against flat portion 37 of plunger rod 20 so that rotation of knob 26 and outer shaft 24 does not cause plunger rod 20 to rotate, but that plunger rod 20 may freely reciprocate within barrel 16. Barrel 16 contains notched portion 28 into which cartridge 12 is received so that tip 22 of plunger rod 20 reciprocates within bore 30 of cartridge 12.

As best seen in FIGS. 2 and 3, ball lock ring 18 contains a plurality of balls 34 sized to fit within groove 32 of outer shaft 24. Ring 18 also contains a plurality release angles 36 opposite groove 32 corresponding to the location of balls 34. As shown in FIG. 2, rotating ball lock ring 18 counter-clockwise forces balls 34 into groove 32 and prevents plunger rod 20 from being advanced by pushing on knob 26. Instead, turning of knob 26 causes balls 34 to ride within groove 32 of grooved outer shaft 24, thereby threadedly pushing or pulling on proximal end 23 of plunger rod and causing corresponding reciprocation of tip 22 of plunger rod 20 within bore 30 of cartridge 12. As best seen in FIG. 3, rotating ball lock ring 18 clockwise forces balls 34 out of groove 32 and allows plunger rod 20 to be advanced by pushing on knob 26. Index pin 38 and slot 40 prevent over-rotation of ball lock ring 18.

While certain embodiments of the present invention have been described above, these descriptions are given for purposes of illustration and explanation. Variations, changes, modifications and departures from the systems and methods disclosed above may be adopted without departure from the scope or spirit of the present invention.

We claim:

1. An intraocular lens delivery system, comprising:
   a) a cartridge having a bore;
   b) a handpiece, the handpiece having a notched portion for receiving the cartridge;
   c) a plunger coaxially received in the handpiece, the plunger having a distal tip and a proximal end opposite the distal tip, the tip reciprocating within the bore of the cartridge when the cartridge is received in the notched portion of the handpiece;
   d) a grooved outer shaft received on the proximal end of the plunger, the grooved outer shaft having a knob rigidly attached thereon;

e) a ball lock ring rotationally mounted on the handpiece, the ball lock ring having a plurality of locking balls that ride within the groove of the outer shaft; and f) a plurality of release angles in the ball lock ring corresponding to the locking balls, the release angles alternatively forcing the locking balls into and out of the groove in the outer shaft in response to rotation of the ball lock ring as the knob is turned, wherein the plunger is slidably advanceable to a distalmost injection position of slidable advancement by pushing the knob when the locking balls are out of the groove and the plunger is threadedly advanceable to the distalmost injection position of slidable advancement by turning the knob when the locking balls are in the groove allowing the intraocular lens to be selectively injected either by slidable or threaded advancement.

2. The lens delivery system of claim 1 wherein forcing the locking balls out of the groove in the outer shaft allows the plunger to be pushed within the handpiece.

3. The lens delivery system of claim 1 wherein rotation of the grooved outer shaft causes the plunger to reciprocate within the handpiece.

* * * * *